United States Patent
Brun

(10) Patent No.: US 7,942,937 B2
(45) Date of Patent: May 17, 2011

(54) PROCESS FOR DYEING THE HAIR USING A COMPOSITION COMPRISING AT LEAST ONE HYDROPHOBIC FILM-FORMING POLYMER, AT LEAST ONE PIGMENT, AND AT LEAST ONE VOLATILE SOLVENT

(75) Inventor: Gaëlle Brun, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/334,773

(22) Filed: Dec. 15, 2008

(65) Prior Publication Data

US 2009/0151086 A1    Jun. 18, 2009

Related U.S. Application Data

(60) Provisional application No. 61/006,486, filed on Jan. 16, 2008.

(30) Foreign Application Priority Data

Dec. 13, 2007 (FR) ..................... 07 59814

(51) Int. Cl.
*A61Q 5/10* (2006.01)
(52) U.S. Cl. ............. 8/405; 8/435; 8/469; 8/476; 8/531; 8/552

(58) Field of Classification Search ............. 8/405, 435, 8/469, 476, 531, 552
See application file for complete search history.

(56) References Cited

U.S. PATENT DOCUMENTS

| | | | |
|---|---|---|---|
| 6,073,635 A | 6/2000 | Todd | |
| 6,106,577 A * | 8/2000 | Audousset et al. | 8/403 |
| 2005/0031656 A1 | 2/2005 | Pays et al. | |
| 2007/0174974 A1* | 8/2007 | De La Mettrie | 8/405 |
| 2007/0245500 A1 | 10/2007 | Brun et al. | |
| 2007/0261179 A1* | 11/2007 | Dorkel et al. | 8/441 |

FOREIGN PATENT DOCUMENTS

| | | |
|---|---|---|
| FR | 2 853 528 | 10/2004 |
| FR | 2 899 804 | 10/2007 |
| WO | WO 2006/057071 | 6/2006 |

OTHER PUBLICATIONS

French Search Report for FR 07/59814, dated Jul. 31, 2008.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The process of the present disclosure comprises applying to the hair at least one composition comprising at least one hydrophobic film-forming polymer, at least one pigment, and at least one volatile solvent, and heating the hair covered with the composition at a temperature above 40° C.

12 Claims, No Drawings

PROCESS FOR DYEING THE HAIR USING A COMPOSITION COMPRISING AT LEAST ONE HYDROPHOBIC FILM-FORMING POLYMER, AT LEAST ONE PIGMENT, AND AT LEAST ONE VOLATILE SOLVENT

This application claims benefit of U.S. Provisional Application No. 61/006,486, filed Jan. 16, 2008, the contents of which are incorporated herein by reference. This application also claims benefit of priority under 35 U.S.C. §119 to French Patent Application No. FR 0759814, filed Dec. 13, 2007, the contents of which are also incorporated herein by reference.

Disclosed herein is a process for dyeing the hair, using at least one hydrophobic film-forming polymer and at least one pigment.

It is known practice to dye keratin fibers via various techniques using direct dyes or pigments for non-permanent dyeing, or dye precursors for permanent dyeing.

Non-permanent dyeing or direct dyeing includes dyeing keratin fibers with dye compositions containing direct dyes. These dyes are colored and are coloring molecules that have affinity for keratin fibers. They are applied to the keratin fibers for the time required to obtain the desired coloration, and are then rinsed out.

The standard dyes that are used include dyes of the nitrobenzene, anthraquinone, nitropyridine, azo, xanthene, acridine, azine, or triarylmethane type, or natural dyes.

Some of these dyes may be used under lightening conditions, which enables the production of colorations that are visible on dark hair.

It is also known practice to dye keratin fibers permanently via oxidation dyeing. This dyeing technique includes applying to the keratin fibers a composition containing dye precursors such as oxidation bases and couplers. These precursors, under the action of an oxidizing agent, form at least one colored substance in the hair.

The variety of molecules used as oxidation bases and couplers can allow a wide range of colors to be obtained, and the colorations resulting therefrom can be permanent, strong, and resistant to external agents, such as light, bad weather, washing, perspiration, and rubbing.

In order to be visible on dark hair, these two dyeing techniques generally involve prior or simultaneous bleaching of the keratin fibers. This bleaching step, performed with an oxidizing agent such as hydrogen peroxide or persalts, can result in appreciable degradation of the keratin fibers, which impairs their cosmetic properties. The hair then has a tendency to become coarse, more difficult to disentangle, and more brittle.

Another dyeing method involves using pigments. The use of pigments at the surface of the keratin fibers generally makes it possible to obtain visible colorations on dark hair, since the surface pigment masks the natural color of the fiber. The use of pigments for dyeing keratin fibers is described, for example, in French Patent Application Publication No. FR 2 741 530, which discusses using, for the temporary dyeing of keratin fibers, a composition comprising at least one dispersion of film-forming polymer particles comprising at least one acid functional group and at least one pigment dispersed in the continuous phase of the said dispersion.

The colorations obtained via this dyeing method can have the drawback of having poor resistance to shampoo washing.

It is, moreover, known practice to produce colored coatings on hair using a composition comprising an electrophilic monomer of cyanoacrylate type, and a pigment, such as those described in European Patent Application Publication No. EP 1 649 898. Such a composition can allow perfectly coated and non-greasy hair to be obtained. However, the coating obtained may not be entirely satisfactory with regard to external agents such as washing and perspiration. Moreover, the coating obtained is sensitive to fatty substances such as sebum.

Thus, there is a need in the art for a process for dyeing keratin fibers such as the hair, which makes it possible to obtain colored coatings that can be color-fast with respect to shampoo and to the various attacking factors to which hair may be subjected, without degrading the keratin fibers, and while keeping the hairs as perfectly individualized as possible.

Accordingly, one aspect of the present disclosure is a process for dyeing the hair, comprising applying to the hair at least one composition comprising at least one hydrophobic film-forming polymer, at least one pigment, and at least one volatile solvent, and heating the hair covered with the composition at a temperature above 40° C.

The process as disclosed herein can produce on keratin fibers colored coatings that make it possible to obtain a shampoo-fast visible coloration on all hair types, while at the same time preserving the physical qualities of the keratin fibers. Such a coating can be resistant to at least one of the external attacking factors to which hair may be subjected, such as blow-drying and perspiration. It can make it possible, for example, to obtain a smooth, uniform deposit. Moreover, it has been observed, surprisingly, that the hairs can remain individualized and can be styled without problem, and that the styling properties afforded to the fibers can be shampoo-fast.

The term "individualized hairs" means hairs which, after application of the composition and drying, are not stuck together, or are separate from each other, and therefore do not form clumps of hair, since the coating is formed around virtually every hair.

According to the present disclosure, the composition comprises at least one hydrophobic film-forming polymer, at least one pigment, and at least one volatile solvent.

For the purposes of the present disclosure, the term "polymer" means a compound corresponding to the repetition of at least one unit (these units being derived from compounds known as monomers). These units are repeated at least twice and, for example, at least three times.

The term "hydrophobic polymer" means a polymer that has a solubility in water at 25° C. of less than 1% by weight.

The term "film-forming" polymer means a polymer that is capable, by itself or in the presence of an auxiliary film-forming agent, of forming a macroscopically continuous film on a support, such as on keratin materials, and for example a cohesive film.

In at least one embodiment of the present disclosure, the at least one hydrophobic film-forming organic polymer is chosen from:

film-forming polymers that are soluble in an organic solvent medium, for instance liposoluble polymers; i.e., the polymer is soluble or miscible in the organic medium and forms a single homogeneous phase when it is incorporated into the medium;

film-forming polymers that are dispersible in an organic solvent medium, which means that the polymer forms an insoluble phase in the organic medium, the polymer remaining stable and/or compatible once incorporated into this medium. For example, such polymers may be in the form of non-aqueous dispersions of polymer particles, such as dispersions in silicone oils or hydrocarbon-based oils; in at least one embodiment of the present disclosure, the non-aqueous polymer dispersions comprise polymer particles stabilized on their surface with at least one stabilizer; these non-aqueous dispersions are often referred to as NADs;

film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizer. These polymer particles are often referred to as lattices; in this case, the composition must comprise at least one aqueous phase.

Among the hydrophobic film-forming polymers that may be used in the composition of the present disclosure, non-limiting mention may be made of synthetic polymers, of radical type or of polycondensate type, polymers of natural origin, and mixtures thereof. Among these hydrophobic film-forming polymers, further non-limiting mention may be made of acrylic polymers, polyurethanes, polyesters, polyamides, polyureas, cellulose-based polymers such as nitrocellulose, silicone polymers, polyamide polymers and copolymers, and polyisoprenes.

The at least one film-forming polymer may be chosen from the film-forming polymers described in International Patent Application Publication No. WO 04/028 487.

The at least one hydrophobic film-forming polymer may be chosen from, for example:

a) homopolymers and copolymers of olefins; cycloolefins; butadiene; isoprene; styrene; vinyl ethers, esters, or amides; (meth)acrylic acid esters or amides containing a linear, branched, or cyclic C1-C20 alkyl group, a C6-C10 aryl group or a C2-C6 hydroxyalkyl group.

Such homopolymers and copolymers may be obtained from monomers chosen from isooctyl(meth)acrylate, isononyl(meth)acrylate, 2-ethylhexyl(meth)acrylate, lauryl (meth)acrylate, isopentyl(meth)acrylate, n-butyl(meth)acrylate, isobutyl(meth)acrylate, ethyl(meth)acrylate, methyl (meth)acrylate, tert-butyl(meth)acrylate, tridecyl(meth) acrylate, stearyl(meth)acrylate, hydroxyethyl(meth)acrylate, 2-hydroxypropyl(meth)acrylate, benzyl acrylate, phenyl acrylate, and mixtures thereof. Amides of the acid monomers that non-limiting mention may be made of include (meth) acrylamides, such as N-alkyl(meth)acrylamides, for example of a C2-C12 alkyl, such as N-ethylacrylamide, N-t-butylacrylamide, and N-octylacrylamide; N-di(C1-C4)alkyl(meth) acrylamides and perfluoroalkyl(meth)acrylates. The above polymers may also contain as monomers small amounts of an unsaturated carboxylic or sulfonic acid such as acrylic acid, methacrylic acid or AMPS, so long as the overall nature of the polymer remains hydrophobic.

As other vinyl monomers that may be used, non-limiting mention may also be made of:

N-vinylpyrrolidone, vinylcaprolactam, vinyl N—(C1-C6) alkylpyrroles, vinyloxazoles, vinylthiazoles, vinylpyrimidines, and vinylimidazoles, olefins such as ethylene, propylene, butenes, isoprene, and butadienes.

The vinyl polymer may be crosslinked using at least one difunctional monomer, for example comprising at least two ethylenic unsaturations, such as ethylene glycol dimethacrylate or diallyl phthalate.

Non-limiting mention will be made, for example, of the alkyl acrylate/cycloalkyl acrylate copolymer sold by Phoenix Chem. under the name GIOVAREZ AC-5099 ML, the acrylates/C12-22 alkyl methacrylate copolymer sold by Rohm & Haas under the name SOLTEX OPT and vinylpyrrolidone copolymers, such as copolymers of a C2-C30 alkene, such as a C3-C22 alkene, and combinations thereof. As examples of VP copolymers that may be used according to the present disclosure, non-limiting mention may also be made of the VP/vinyl laurate copolymer, the VP/vinyl stearate copolymer, the butylated polyvinylpyrrolidone (PVP) copolymer, the VP/hexadecene copolymer sold by ISP under the name GANEX V216, the VP/eicosene copolymer sold by ISP under the name GANEX V220, the VP/triacontene copolymer or the VP/acrylic acid/lauryl methacrylate copolymer. Non-limiting mention may also be made of the copolymers whose CTFA name (4th edition, 1991) is octylacrylamide/acrylates/ butylaminoethyl methacrylate copolymer, such as the products sold under the name AMPHOMER® or LOVOCRYL® 47 by the company National Starch, and also the copolymers whose CTFA name is acrylates/octylacrylamide copolymer, such as the products sold under the name DERMACRYL® LT or DERMACRYL® 79 by the company National Starch.

Polymers of which non-limiting mention may be made include:

i) polymers bearing fluoro groups belonging to one of the classes described in the above text, for example the FOMBLIN products described in U.S. Pat. No. 5,948,393, and the copolymers of alkyl(meth)acrylate/perfluoroalkyl(meth) acrylate described in European Patent No. EP 0 815 836 and U.S. Pat. No. 5,849,318.

ii) polymers or copolymers resulting from the polymerization or copolymerization of an ethylenic monomer, comprising at least one ethylenic bond, which can be, for example, conjugated (or dienes). As polymers or copolymers resulting from the polymerization or copolymerization of an ethylenic monomer, it is possible to use vinyl, acrylic, or methacrylic copolymers.

In at least one embodiment of the present disclosure, the at least one film-forming polymer is a block copolymer comprising at least one block comprising styrene units or styrene derivatives (for example methylstyrene, chlorostyrene, or chloromethylstyrene). The copolymer comprising at least one styrene block may be, for example, a diblock or triblock copolymer, or even a multiblock, star, or radial copolymer. The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block constituted of styrene units or styrene derivatives may be a diblock or triblock copolymer, for example of the polystyrene/polyisoprene or polystyrene/polybutadiene type, such as those sold or manufactured under the name LUVITOL HSB by BASF and those of the polystyrene/copoly(ethylene-propylene) type or alternatively of the polystyrene/copoly(ethylene/butylene) type, such as those sold or manufactured under the brand name KRATON by Shell Chemical Co. or GELLED PERMETHYL 99A by Penreco.

Non-limiting mention may be made, for example, of KRATON G1650 (SEBS), KRATON G1651 (SEBS), KRATON G1652 (SEBS), KRATON G1657X (SEBS), KRATON G1701X (SEP), KRATON G1702X (SEP), KRATON G1726X (SEB), KRATON D-1101 (SBS), KRATON D-1102 (SBS), KRATON D-1107 (SIS), GELLED PERMETHYL 99A-750, GELLED PERMETHYL 99A-753-58 (mixture of star block polymer and of triblock polymer), GELLED PERMETHYL 99A-753-59 (mixture of star block polymer and of triblock polymer), VERSAGEL MD 970 and VERSAGEL MD 960 from Penreco (mixture of star polymer and of triblock polymer in isododecane).

Styrene-methacrylate copolymers may also be used, such as the polymers sold under the references OS 129880, OS 129881, and OS 84383 from Lubrizol (styrene-methacrylate copolymer).

In at least one embodiment of the present disclosure, the at least one film-forming polymer is chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer chosen from vinyl esters (other than the vinyl ester already present), α-olefins (containing from 8 to 28 carbon atoms), alkyl vinyl ethers (in which the alkyl group contains from 2 to 18 carbon atoms), or allylic or methallylic esters (containing a linear or branched saturated hydrocarbon-based radical of 1 to 19 carbon atoms, bonded to the carbonyl of the ester group).

These copolymers may be partially crosslinked using crosslinking agents that may be either of the vinyl type or of the allylic or methallylic type, such as tetraallyloxyethane, divinylbenzene, divinyl octanedioate, divinyl dodecanedioate, and divinyl octadecanedioate.

Non-limiting examples of these copolymers include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate crosslinked with 0.2% divinylbenzene.

iii) polyalkenes and copolymers of C2-C20 alkenes, for example polybutene.

iv) polymers of natural origin, which are optionally modified, chosen from shellac resin, sandarac gum, dammar resins, elemi gums, copal resins, and polysaccharides comprising alkyl (ether or ester) side chains, for example alkylcelluloses containing a linear or branched, saturated, or unsaturated C1-C8 alkyl radical, such as ethylcellulose and propylcellulose.

The at least one film-forming polymer of natural origin may be chosen, for example, from cellulose-based polymers such as nitrocellulose, cellulose acetate, cellulose acetobutyrate, or cellulose acetopropionate. Non-limiting examples include the ethylcellulose sold by Aqualon under the reference QUALNO ETHYLCELLULOSE N200, the cellulose acetobutyrate sold by Eastman Chemical under the reference CAB-381-0.5, and the cellulose acetopropionates sold by Eastman Chemical under the references CAP-482-20 and CAP-504-0.2.

v) polycondensates

Among the polycondensates that may be used, non-limiting mention may also be made are nonionic polyurethanes, polyurethane-acrylics, polyurethane-polyvinylpyrrolidones, polyester-polyurethanes, polyether-polyurethanes, polyureas, polyurea-polyurethanes, and mixtures thereof.

The polyurethanes may be, for example, a copolymer of aliphatic, cycloaliphatic, or aromatic polyurethane, or of polyurea-polyurethane.

The polyurethanes as defined in the present disclosure may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting mention may also be made of polyesters, polyester amides, fatty-chain polyesters, polyamides, and epoxyester resins.

The polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol, and 4,4-N-(1-methylpropylidene)bisphenol may be used as aliphatic diols.

The polyesteramides may be obtained in a manner similar to that for the polyesters, via the polycondensation of diacids with amino alcohols. The polyamides may be obtained in a manner similar to that for the polyesters, via the polycondensation of diacids with diamines.

For example, polyesters that may be mentioned include aliphatic polyesters containing C4-50 alkyl side chains or polyesters resulting from the condensation of fatty acid dimers, or alternatively polyesters comprising a silicone segment in the form of a terminal block, graft, or group, as defined in French Patent Application No. FR 0 113 920.

b) Silicone compounds.

The at least one hydrophobic film-forming polymer may also comprise at least one silicone portion.

In the present disclosure, in accordance with what is generally accepted, the terms "silicone" and "polysiloxane" mean any organosilicon polymer or oligomer of linear, cyclic, branched, or crosslinked structure, of variable molecular weight, obtained by polymerization and/or polycondensation of suitably functionalized silanes, and constituted essentially of a repetition of main units in which the silicon atoms are linked together via oxygen atoms (siloxane bond $\equiv$Si—O—Si$\equiv$), optionally substituted hydrocarbon-based radicals being bonded directly via a carbon atom to the silicon atoms. The most common hydrocarbon-based radicals are alkyl radicals, such as of C1-C10 and, for example, methyl, fluoroalkyl radicals, aryl radicals, and, for example, phenyl, alkenyl, and vinyl radicals; other types of radicals that may be bonded, either directly or via a hydrocarbon-based radical, to the siloxane chain are, for example, hydrogen, halogens such as chlorine, bromine, fluorine, thiols, alkoxy radicals, polyoxyalkylene (or polyether) radicals such as polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulfosuccinates, thiosulfates, phosphates, and sulfates, this list not being in any way limiting ("organomodified" silicones).

Among the at least one hydrophobic film-forming polymer comprising at least one silicone portion, non-limiting mention may be made of:

i) silicone resins, which are generally soluble or swellable in silicone oils.

These resins are crosslinked polymers of polyorganosiloxanes.

The nomenclature of silicone resins is known under the name MDTQ, the resin being described as a function of the various siloxane monomer units it comprises, each of the letters MDTQ characterizing a type of unit.

The letter M represents the monofunctional unit of formula $(CH_3)_3SiO_{1/2}$, the silicon atom being connected to only one oxygen atom in the polymer comprising this unit.

The letter D represents a difunctional unit $(CH_3)_2SiO_{2/2}$ in which the silicon atom is connected to two oxygen atoms.

The letter T represents a trifunctional unit of formula $(CH_3)SiO_{3/2}$.

In the units M, D, and T defined previously, at least one of the methyl groups may be substituted with a group R other than a methyl group, such as a hydrocarbon-based radical (for example alkyl) containing from 2 to 10 carbon atoms or a phenyl group, or alternatively a hydroxyl group.

Finally, the letter Q represents a tetrafunctional unit $SiO_{4/2}$ in which the silicon atom is bonded to four hydrogen atoms, which are themselves bonded to the rest of the polymer.

Various resins with different properties may be obtained from these different units, the properties of these polymers varying as a function of the type of monomers (or units), of the type and number of substituted radicals, of the length of the polymer chain, of the degree of branching, and of the size of the side chains.

Examples of these silicone resins of which non-limiting mention may be made include:
- siloxysilicates, which may be trimethyl siloxysilicates of formula $[(CH_3)_3.Si.O]_x.(SiO_{4/2})_y$ (units MQ) in which x and y are integers ranging from 50 to 80,
- polysilsesquioxanes of formula $(CH_3SiO_{3/2})_x$ (units T) in which x is greater than 100 and in which at least one of the methyl radicals may be substituted with a group R as defined above,
- polymethylsilsesquioxanes, which are polysilsesquioxanes in which none of the methyl radicals are substituted with another group. Such polymethylsilsesquioxanes are described in U.S. Pat. No. 5,246,694.

Non-limiting examples of commercially available polymethylsilsesquioxane resins that may be mentioned include those sold:
- by the company Wacker under the reference RESIN MK, such as BELSIL PMS MK: polymer comprising $CH_3SiO_{3/2}$ repeating units (units T), which may also comprise up to 1% by weight of $(CH_3)_2SiO_{2/2}$ units (units D), and having an average molecular weight of about 10,000,
- by the company Shin-Etsu under the references KR-220L, which are compounds of units T of formula $CH_3SiO_{3/2}$ and have Si—OH (silanol) end groups, under the reference KR-242A, which comprise 98% of units T and 2% of dimethyl units D and have Si—OH end groups, or alternatively under the reference KR-251, comprising 88% of units T and 12% of dimethyl units D, and have Si—OH end groups.

Siloxysilicate resins of which non-limiting mention may be made of trimethyl siloxysilicate (TMS) resins, for example in the form of powders. Such resins are sold under the reference SR1000 by the company General Electric or under the reference TMS 803 by the company Wacker. Non-limiting mention may also be made of the trimethyl siloxysilicate resins sold in a solvent such as cyclomethicone, sold under the name KF-7312J by the company Shin-Etsu or DC 749 or DC 593 by the company Dow Corning.

ii) Silicone polyamides of the polyorganosiloxane type such as those described in U.S. Pat. Nos. 5,874,069, 5,919,441, 6,051,216, and 5,981,680.

iv) Grafted silicone compounds

The composition of the present disclosure may also contain a grafted silicone polymer. In the context of the present disclosure, the term "grafted silicone polymer" means a polymer comprising a polysiloxane portion and a portion constituted of a non-silicone organic chain, one of the two portions constituting the main chain of the polymer, the other being grafted onto the main chain.

The grafted silicone polymers used in the cosmetic composition according to the present disclosure can be chosen from, by way of non-limiting example, including polymers with a non-silicone organic backbone grafted with monomers containing a polysiloxane, polymers with a polysiloxane backbone grafted with non-silicone organic monomers, and mixtures thereof.

The non-silicone organic monomers constituting the main chain of the grafted silicone polymer may be chosen from radical-polymerizable ethylenically unsaturated monomers, polycondensation-polymerizable monomers such as those forming polyamides, polyesters or polyurethanes, and ring-opening monomers such as those of the oxazoline or caprolactone type.

The polymers containing a non-silicone organic backbone grafted with monomers containing a polysiloxane, in accordance with the present disclosure, may be chosen from, by way of non-limiting example, those described in U.S. Pat. Nos. 4,693,935, 4,728,571, and 4,972,037, and Patent Publication Nos. EP A 0 412 704, EP A 0 412 707, EP A 0 640 105, and WO 95/00578. They are copolymers obtained by radical polymerization starting with ethylenically unsaturated monomers and silicone macromers containing a vinyl end group, or alternatively copolymers obtained by reacting a polyolefin comprising functionalized groups with a polysiloxane macromer containing an end functional group that is reactive with the functionalized groups.

The polymer containing a non-silicone organic backbone grafted with monomers containing a polysiloxane may, for example, have the following structure:

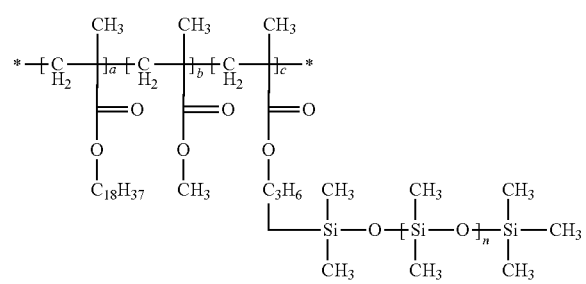

Such a polymer is sold under the name KP 561 by Shin-Etsu.

The copolymer containing a non-silicone organic backbone grafted with monomers containing a polysiloxane may also have the following structure:

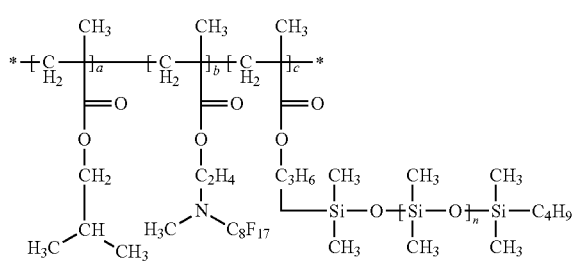

Such a polymer, Polysilicone 7, is sold under the name SA70 by 3M.

Other copolymers containing a non-silicone organic backbone grafted with monomers containing a polysiloxane may also be KP545, KP574, and KP575 sold by Shin-Etsu.

A grafted silicone compound that may also be mentioned is the isobutyl methacrylate/bis-hydroxypropyl dimethicone acrylate copolymer sold by Grant Industries under the name GRANACRYSIL BMAS.

According to the present disclosure, the grafted silicone polymer, containing a polysiloxane backbone grafted with non-silicone organic monomers, comprises a main silicone chain (or polysiloxane ($\equiv$Si—O—)$_n$) onto which is grafted, within the chain and also optionally on at least one of its ends, at least one organic group not comprising silicone.

Non-limiting examples of silicone polymers corresponding to the definition include polydimethylsiloxanes (PDMS) onto which are grafted, via a connecting chain unit of thiopropylene type, mixed polymer units of the poly(meth)acrylic acid type and of the polyalkyl(meth)acrylate type. A compound corresponding to this definition of which non-limiting mention may be made is the poly dimethyl/methyl siloxane containing methyl 3-thiopropyl acrylate/methyl methacrylate/methacrylic acid groups, or Polysilicone-8 sold under the name VS80 by the company 3M.

Other non-limiting examples of silicone polymers include polydimethylsiloxanes (PDMS) onto which are grafted, via a connecting chain unit of thiopropylene type, polymer units of the polyisobutyl(meth)acrylate type.

For example, the number-average molecular mass of the silicone polymers containing a polysiloxane backbone grafted with non-silicone organic monomers of the present disclosure ranges from 10,000 to 1,000,000, for example from 10,000 to 100,000.

For example, the grafted silicone polymers can be chosen from the copolymers of polydimethylsiloxane-grafted alkyl methacrylate, copolymers of isobutyl methacrylate, of acrylic acid and of silicone macromer, and the poly dimethyl/methyl siloxane containing methyl 3-thiopropyl acrylate/methyl methacrylate/methacrylic acid groups.

v) Polyurea/urethane silicones

The at least one copolymer of the present disclosure may comprise, in addition to the polysiloxane/polyurea, other blocks of different units. Non-limiting mention will be made of polysiloxane/polyurea/polyurethane block terpolymers.

According to at least one embodiment, the at least one copolymer contains only at least one siloxane block and at least one polyurea block.

According to the present disclosure, the at least one copolymer may be chosen from those of formula (I):

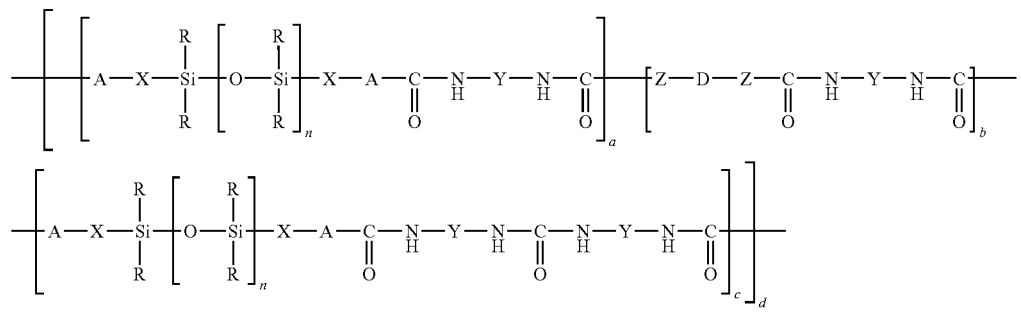

wherein:

R is a monovalent hydrocarbon-based radical, optionally substituted with fluorine or chlorine, containing 1 to 20 carbon atoms, X is an alkylene radical containing 1 to 20 carbon atoms, in which non-neighboring methylene units may be replaced with —O— radicals, A is an oxygen atom or an amino radical —NR'—, Z is an oxygen atom or an amino radical —NR'—, R' is hydrogen or an alkyl radical containing 1 to 10 carbon atoms, Y is a divalent hydrocarbon-based radical, optionally substituted with fluorine or chlorine, containing 1 to 20 carbon atoms, D is an alkylene radical, optionally substituted with fluorine, chlorine, C1-C6 alkyl or C1-C6 alkyl ester, containing from 1 to 700 carbon atoms, in which non-neighbouring methylene units may be replaced with radicals —O—, —COO—, —OCO— or —OCOO—, n is a number ranging from 1 to 4,000,
a is a number at least equal to 1,
b is a number ranging from 0 to 40,
c is a number ranging from 0 to 30, and
d is a number greater than zero,
on the condition that A is an NH radical in at least one of the units (a).

For example, R can be a monovalent hydrocarbon-based radical of 1 to 6 carbon atoms, for example methyl, ethyl, vinyl, and phenyl. According to at least one embodiment of the present disclosure, R is an unsubstituted alkyl radical.

For example, X can be an alkylene radical containing 2 to 10 carbon atoms. For example, in at least one embodiment, the alkylene radical X is not interrupted.

According to at least one embodiment of the present disclosure, the group A in all the units (b) and (c), when they are present, is NH.

According to at least one embodiment of the present disclosure, all the groups A represent an NH radical.

For example, Z can be an oxygen atom or an NH radical.

For example, Y can be a hydrocarbon-based radical containing from 3 to 13 carbon atoms, which is, for example, unsubstituted. For example, Y can be a linear or cyclic aralkylene or alkylene radical.

For example, D can be an alkylene radical containing at least 2 and, for example, at least 4 carbon atoms, and not more than 12 carbon atoms.

Also for example, D can be a polyoxyalkylene radical, for example a polyoxyethylene or polyoxypropylene radical containing at least 20, such as at least 100, carbon atoms, and not more than 800 such as not more than 200 carbon atoms.

For example, in at least one embodiment the radical D is unsubstituted.

For example, n may represent a number equal to at least 3 such as at least 25, and for example not more than 800, such as not more than 400 and, for example, not more than 250.

For example, a can be a number greater than 50.

When b is other than 0, b can be a number not greater than 50 and, for example, not greater than 25.

For example, c can be a number not greater than 10 and, for example, not greater than 5.

The copolymers of the present disclosure may be obtained according to the polymerization processes described in U.S. Patent Application Publication No. 2004/0254325 or International Patent Application Publication No. WO 03/014194.

According to at least one embodiment of the present disclosure, the at least one copolymer is a nonionic polysiloxane/polyurea copolymer, i.e. it does not contain any ionized or ionizable groups.

A non-limiting example of a copolymer that may be mentioned is the dimethylpolysiloxane/urea copolymer, of INCI name polyurea dimethicone.

Such a polymer may be obtained, for example, by copolymerization of an α,ω-aminosilicone with a diisocyanate. Polymers corresponding to these characteristics are, for example, the products sold under the references WACKER-BELSIL® UD 60, WACKER-BELSIL® UD 80, WACKER-BELSIL® UD 140 and WACKER-BELSIL® UD 200 by the company Wacker.

vi) Copolymers based on silicone resin and on fluid silicone

These silicone copolymers are obtained by reacting a silicone resin and a fluid silicone.

Such copolymers are described, for example, in *Silicone Pressure Sensitive Adhesive*, Sobieski and Tangney, Handbook of Pressure Sensitive Adhesive Technology (D. Satas Ed.), von Nostrand Reinhold, New York.

In the copolymer, the silicone resin is present in an amount ranging from 45% to 75% (relative to the total mass of silicone) and the fluid silicone is present in an amount ranging from 25% to 55%, with the sum of the percentages of silicone resin and of fluid silicone being equal to 100. For example, the silicone resin may be present in an amount ranging from 55% to 65% (relative to the total mass of silicone) and the fluid silicone may be present in an amount ranging from 35% to 45%, with the sum of the percentages of silicone resin and of fluid silicone being equal to 100.

For example, the silicone resin according to the present disclosure can be the product of condensation of $SiO_2$ groups and of $R3(SiO)_{1/2}$ (triorganosilyl) groups for which each group R is independently selected from methyl, ethyl, propyl, and vinyl radicals and for which the ratio between the $SiO_2$ functional groups and the $R3(SiO)_{1/2}$ functional groups of the silicone resin ranges from 0.6 to 0.9. Triorganosilyl groups that may be used to form the silicone resin may be trimethylsilyl, triethylsilyl, methylmethylpropylsilyl, dimethylvinylsilyl units, and mixtures thereof. In at least one embodiment of the present disclosure the trimethylsilyl group is used.

For example, the fluid silicone according to the present disclosure can be a diorganopolysiloxane containing OH end functional groups, having a viscosity ranging from 100 to 100,000 cSt at 25° C., for which the substituents of the diorganopolysiloxane are chosen independently from methyl, ethyl, propyl, and vinyl radicals. The diorganosiloxanes may be, for example, linear polymers. Examples of diorganopolysiloxanes may be, in a non-limiting manner, a polydimethylsiloxane, an ethylmethylpolysiloxane, the copolymer of dimethylsiloxane and of methylvinylsiloxane, and mixtures of such polymers or copolymers containing OH end groups. The diorganopolysiloxane may be a polydimethylsiloxane.

Examples of synthesis of such a copolymer are described, for example, in U.S. Pat. No. 5,162,410 or in Canadian Patent Publication No. 711 756.

Non-limiting examples of the copolymers according to the present disclosure include those sold by Dow Corning under the reference BIO-PSA®, these BIO-PSA® copolymers themselves possibly being in two forms, standard or amine-compatible, and being supplied in different solvents with several silicone resin/fluid silicone ratios. Non-limiting mention may be made of the grades 7-4400, 7-4500, and 7-4600. In at least one embodiment, the BIO-PSA® that is used according to the present disclosure may be the grade 7-4400.

vii) Reactive silicones

The at least one hydrophobic film-forming polymer may be chosen from polymers obtained from silicone compounds X and Y that are capable of reacting together at the time of application to form the at least one hydrophobic film-forming polymer. As used herein, the term "silicone compound" means a compound comprising at least two organosiloxane units. According to at least one embodiment of the present disclosure, the compounds X and the compounds Y are silicone compounds. The compounds X and Y may be amino or non-amino compounds. They may comprise polar groups that may be chosen from the following groups: —COOH, —COO$^-$, —COO—, —OH, —NH$_2$, —NH—, —NR—, —SO$_3$H, —SO$_3$$^-$, —OCH$_2$CH$_2$—, —O—CH$_2$CH$_2$CH$_2$—, —O—CH$_2$CH(CH$_3$)—, —NR$_3$$^+$, —SH, —NO$_2$, I, Cl, Br, —CN, —PO$_4$$^{3-}$, —CONH—, —CONR—, —CONH$_2$, —CSNH—, —SO$_2$—, —SO—, —SO$_2$NH—, —NHCO—, —NHSO$_2$—, —NHCOO—, —OCONH—, —NHCSO—, and —OCSNH—, R representing an alkyl group.

According to at least one embodiment of the present disclosure, at least one of the compounds X and Y is a polymer whose main chain is mainly formed from organosiloxane units.

Among the silicone compounds mentioned hereinbelow, some of them may have both film-forming properties and adhesive properties, depending, for example, on the silicone proportion thereof or on whether they are used as a mixture with an additive. It is possible to modify the film-forming properties or the adhesive properties of such compounds according to the intended use, and this is, for example, in the case for the reactive elastomeric silicones known as room-temperature-curable silicones.

Compounds X and Y can react together at a temperature ranging from room temperature to 180° C. For example, compounds X and Y may be capable of reacting together at room temperature (20±5° C.) and atmospheric pressure, such as in the presence of a catalyst, via a hydrosilylation reaction or a condensation reaction, or a crosslinking reaction in the presence of a peroxide.

By way of non-limiting example of a combination of compounds X and Y that react via hydrosilylation, mention may be made of the following references proposed by the company Dow Corning: DC 7-9800 SOFT SKIN ADHESIVE parts A & B, and also the following mixtures A and B prepared by Dow Corning:

Mixture A:

| Ingredient (INCI name) | CAS No. | Content (%) | Function |
|---|---|---|---|
| Dimethylsiloxane, Dimethylvinylsiloxy-terminated | 68083-19-2 | 55-95 | Polymer |
| Silica Silylate | 68909-20-6 | 10-40 | Filler |
| 1,3-Diethenyl-1,1,3,3-Tetra-methyldisiloxane complexes | 68478-92-2 | Trace | Catalyst |
| Tetramethyldivinyldisiloxane | 2627-95-4 | 0.1-1 | Polymer |

Mixture B:

| Ingredient (INCI name) | CAS No. | Content (%) | Function |
|---|---|---|---|
| Dimethylsiloxane, Dimethylvinylsiloxy-terminated | 68083-19-2 | 55-95 | Polymer |
| Silica Silylate | 68909-20-6 | 10-40 | Filler |
| Dimethyl, Methylhydrogensiloxane, trimethylsiloxy-terminated | 68037-59-2 | 1-10 | Polymer |

Compounds X and Y are capable of reacting via condensation, either in the presence of water (hydrolysis) by reaction of 2 compounds bearing alkoxysilane groups, or via "direct" condensation by reaction of a compound bearing at least one alkoxysilane group and a compound bearing at least one silanol group or by reaction of 2 compounds each bearing at least one silanol group.

When the condensation is performed in the presence of water, this water may, for example, be provided water by an external source, for example premoistening of the hair (for example with a mister).

In this mode of reaction via condensation, compounds X and Y, which may be identical or different, may thus be chosen from silicone compounds whose main chain comprises at least two alkoxysilane groups and/or at least two silanol (Si—OH) groups, on the side and/or at the end of the chain.

According to at least one embodiment of the present disclosure, compounds X and/or Y are chosen from polyorganosiloxanes comprising at least two alkoxysilane groups. As used herein, the term "alkoxysilane group" means a group comprising at least one —Si—OR portion, R being an alkyl group containing from 1 to 6 carbon atoms.

Compounds X and Y can be, for example, chosen from polyorganosiloxanes comprising alkoxysilane end groups, such as those comprising at least 2 alkoxysilane end groups and, for example, trialkoxysilane end groups.

Such polymers are described, for example, in U.S. Pat. Nos. 3,175,993, 4,772,675, 4,871,827, 4,888,380, 4,898,910, 4,906,719, and 4,962,174, and International Patent Application Publication No. WO 01/96450.

As non-limiting examples of a combination of compounds X and Y bearing alkoxysilane groups and reacting via condensation, mention may be made of the mixtures A' and B' below prepared by the company Dow Corning:

Mixture A':

| Ingredient (INCI name) | CAS No. | Content (%) | Function |
|---|---|---|---|
| Bis-trimethoxysiloxyethyl tetramethyldisiloxyethyl dimethicone (*) | PMN87176 | 25-45 | Polymer |
| Silica silylate | 68909-20-6 | 5-20 | Filler |
| Disiloxane | 107-46-0 | 30-70 | Solvent |

(*) It should be noted that the identical compounds X and Y are combined in the mixture A'.

Mixture B':

| Ingredient (INCI name) | CAS No. | Content (%) | Function |
|---|---|---|---|
| Disiloxane | 107-46-0 | 80-99 | Solvent |
| Tetra-t-butyl titanate | — | 1-20 | Catalyst |

When the at least one film-forming polymer according to the present disclosure is dispersed in the organic solvent, the composition according to the present disclosure comprises at least one stable dispersion of essentially spherical polymer particles of at least one polymer. Before incorporating them into the composition of the present disclosure, the particles are generally dispersed in a physiologically acceptable liquid fatty phase, such as hydrocarbon-based oils or silicone oils. According to at least one embodiment of the present disclosure, these dispersions are generally known as NADs (non-aqueous dispersions) of polymer, as opposed to networks, which are aqueous dispersions of polymer.

These dispersions may be in the form of polymer nanoparticles in stable dispersion in the liquid organic phase. The nanoparticles can have a mean size ranging from 5 to 800 nm, such as ranging from 50 to 500 nm. It is possible, however, to obtain polymer particle sizes ranging up to 1 μm.

The at least one polymer in dispersion that may be used in the composition of the present disclosure may, for example, have a molecular weight ranging from 2,000 to 10,000,000 and a Tg ranging from −100° C. to 300° C. such as from −10° C. to 80° C.

Among the at least one film-forming polymer in dispersion that may be mentioned are radical, acrylic or vinyl homopolymers or copolymers, such as those with a Tg of less than or equal to 40° C. and, for example, ranging from −10° C. to 30° C., used alone or as a mixture.

According to at least one embodiment of the present disclosure, the polymer particles are stabilized with a stabilizer that is solid at room temperature, which may be a block polymer, a grafted polymer, and/or a statistical polymer, alone or as a mixture. The stabilization may be performed via any known techniques, such as by direct addition of the stabilizing polymer during the polymerization.

When an aqueous dispersion of polymer particles is used, the solids content of the aqueous dispersion can range from about 3% to 60% by weight and such as from 10% to 50% by weight.

The size of the polymer particles in aqueous dispersion may range from 10 to 500 nm, for example, ranging from 20 to 150 nm, allowing the production of a film having appreciable gloss. However, particle sizes ranging up to one micron may be used.

In a non-limiting manner, the at least one film-forming polymer can be chosen from the following polymers or copolymers: polyurethanes, polyurethane-acrylics, polyureas, polyurea-polyurethanes, polyester-polyurethanes, polyether-polyurethanes, polyesters, polyester amides; acrylic, and/or vinyl polymers or copolymers; acrylic-silicone copolymers; polyacrylamides; silicone polymers such as silicone polyurethane or acrylic polymers, fluoro polymers; celluloses; and mixtures thereof.

The at least one hydrophobic film-forming polymer according to the present disclosure may be selected on the basis of its mechanical properties. Such properties include the flexibility, the hardness, the adhesion, the remanence, the resistance to water or to other chemical compounds, and the abrasion resistance. It is also possible to take advantage of the more versatile properties of block polymers (polymers comprising at least two distinct polymer segments), grafted polymers (polymers containing a polymeric side chain grafted onto the homopolymer or copolymer backbone), or heteropolymers (polymers comprising at least two different monomers). In the copolymers, for example, the amount of hard and soft blocks has a significant impact on the properties of the polymer.

Furthermore, it is possible to mix at least two polymers in order to achieve the desired property. Non-limiting examples of combinations may be polyurethane and polyacrylates, polyurethane and polyesters, two polymers having a silicone portion, or polyurethane and a polymer having a silicone portion.

According to at least one embodiment of the present disclosure, the at least one hydrophobic film-forming polymer is a nonionic polymer. According to at least one other embodiment of the present disclosure, the at least one film-forming polymer is solid at 25° C., in the sense that no flowing is observed with the naked eye after one hour.

The polymer may be present in the composition in an amount ranging from 0.1% to 40% by weight, such as from 0.1% to 30% by weight, for example ranging from 0.5% to 20% by weight, such as from 1% to 20% by weight, for example ranging from 1% to 15% by weight, relative to the total weight of the composition.

When the glass transition temperature of the polymer is too high for the desired use, at least one plasticizer may be combined therewith so as to lower this temperature of the mixture used. The plasticizer may be chosen from the plasticizers usually used in the field of application, such as from compounds that may be solvents for the polymer.

For example, the at least one plasticizer may have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 100 g/mol.

Thus, the composition may also comprise at least one plasticizer. For example, non-limiting mention may be made, alone or as a mixture, of common plasticizers such as:

glycols and derivatives thereof, such as diethylene glycol ethyl ether, diethylene glycol methyl ether, diethylene glycol butyl ether or diethylene glycol hexyl ether, ethylene glycol ethyl ether, ethylene glycol butyl ether, or ethylene glycol hexyl ether;

polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters;

propylene glycol derivatives such as propylene glycol phenyl ether, propylene glycol diacetate, dipropylene glycol ethyl ether, tripropylene glycol methyl ether, diethylene glycol methyl ether, and dipropylene glycol butyl ether. Such compounds are sold by Dow Chemical under the names DOWANOL PPH and DOWANOL DPnB;

acid esters, for example carboxylic acids, such as citrates, phthalates, adipates, carbonates, tartrates, phosphates, and sebacates;

esters derived from the reaction of a monocarboxylic acid of formula $R_{11}COOH$ with a diol of formula $HOR_{12}OH$ in which $R_{11}$ and $R_{12}$, which may be identical or different, are chosen from a linear, branched or cyclic, saturated, or unsaturated hydrocarbon-based chain containing, for example, from 3 to 15 carbon atoms, optionally comprising at least one heteroatom such as N, O or S, for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical;

oxyethylenated derivatives, such as oxyethylenated oils, such as plant oils, such as castor oil;

mixtures thereof.

For example, the at least one plasticizer may be chosen from esters of at least one carboxylic acid containing 1 to 7 carbon atoms and of a polyol comprising at least 4 hydroxyl groups.

The polyol according to the present disclosure may be a cyclized or uncyclized saccharide-polyhydroxyaldehyde (aldose) or polyhydroxyketone (ketose). For example, the polyol may be a saccharide cyclized in hemiacetal form.

The polyol can be a monosaccharide or a polysaccharide comprising from 1 to 10 saccharides, such as from 1 to 4 saccharides, for example one or two saccharides. The polyol may be chosen from erythritol, xylitol, sorbitol, glucose, sucrose, lactose, and maltose.

The polyol according to the present disclosure may be a disaccharide. Among the disaccharides, non-limiting mention may be made of sucrose (also known as α-D-glucopyranosyl-(1-2)-β-D-fructofuranose), lactose (also known as β-D-galactopyranosyl-(1-4)-β-D-glucopyranose), and maltose (also known as α-D-glucopyranosyl-(1-4)-β-D-glucopyranose), for example sucrose.

The ester according to the present disclosure may be constituted of a polyol esterified with at least two different monocarboxylic acids, or with at least three different monocarboxylic acids.

The ester according to the present disclosure may be a copolymer of two esters, such as a copolymer i) of a sucrose substituted with benzoyl groups and ii) of a sucrose substituted with acetyl and/or isobutyryl groups.

The carboxylic acid may be a monocarboxylic acid containing from 1 to 7 carbon atoms such as from 1 to 5 carbon atoms, chosen, for example, from acetic acid, n-propanoic acid, isopropanoic acid, n-butanoic acid, isobutanoic acid, tert-butanoic acid, n-pentanoic acid, and benzoic acid.

The ester may be obtained from at least two different monocarboxylic acids. According to at least one embodiment of the present disclosure, the acid is an unsubstituted linear or branched acid.

The acid may be chosen from acetic acid, isobutyric acid, benzoic acid, and mixtures thereof.

According to at least one embodiment of the present disclosure, the ester is sucrose diacetate hexakis(2-methylpropanoate), such as the product sold under the name SUSTANE SAIB FOOD GRADE KOSHER by the company Eastman Chemical.

According to at least one other embodiment of the present disclosure, the at least one plasticizer may be chosen from esters of an aliphatic or aromatic polycarboxylic acid and of an aliphatic or aromatic alcohol containing from 1 to 10 carbon atoms.

The aliphatic or aromatic alcohol contains from 1 to 10, such as from 1 to 8 carbon atoms, for example from 1 to 6 carbon atoms. It may be chosen from alcohols R1OH such that R1 may be methyl, ethyl, propyl, isopropyl, butyl, hexyl, ethylhexyl, decyl, isodecyl, benzyl, or benzyl substituted with an alkyl containing 1 to 3 carbon atoms, and mixtures thereof.

The aliphatic or aromatic polycarboxylic acid contains, for example, from 3 to 12 carbon atoms, such as from 3 to 10 carbon atoms, for example from 3 to 8 carbon atoms, such as 6 or 8 carbon atoms.

For example, the aliphatic or aromatic polycarboxylic acid can be chosen from dicarboxylic acids and tricarboxylic acids.

Among the aliphatic dicarboxylic acids of which non-limiting mention may be made are those of formula HOOC—(CH2)n-COOH, in which n is an integer ranging from 1 to 10, such as ranging from 2 to 8, for example equal to 2, 4, 6 or 8.

For example, the dicarboxylic acids may be chosen from succinic acid, adipic acid and sebacic acid.

Among the aromatic dicarboxylic acids, mention may be made of phthalic acid.

Among the tricarboxylic acids, mention may be made of the triacids that correspond to formula

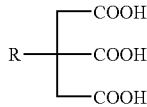

wherein R is a group —H, —OH or —OCOR' wherein R' is an alkyl group containing from 1 to 6 carbon atoms. For example, R can be a group —OCOCH3.

The tricarboxylic acid may be, for example, chosen from acetylcitric acid, butyroylcitric acid, and citric acid.

The tricarboxylic acid esters that may be used include esters derived from citric acid (or citrates) such as tributyl acetyl citrate, triethyl acetyl citrate, triethylhexyl acetyl citrate, trihexyl acetyl citrate, trihexyl butyroyl citrate, triisodecyl citrate, triisopropyl citrate, tributyl citrate, and tris(2-ethylhexyl)citrate. As commercial references of plasticizers mentioned above, mention may be made of the CITROFLEX range sold by Vertellus, especially, CITROFLEX A4 and CITROFLEX C2.

The adipic acid esters that may be used include dibutyl adipate and bis(2-ethylhexyl)adipate.

The sebacic acid esters that may be used include dibutyl sebacate, bis(2-ethylhexyl)sebacate, diethyl sebacate, and diisopropyl sebacate.

The succinic acid esters that may be used include bis(2-ethylhexyl)succinate and diethyl succinate.

The phthalic acid esters that may be used include butyl benzyl phthalate, dibutyl phthalate, diethylhexyl phthalate, diethyl phthalate, and dimethyl phthalate.

The plasticizer may be present in the composition of the present disclosure in an amount such that the mass ratio between the hydrophobic film-forming polymer and the plasticizer ranges from 0.5 to 100, such as ranging from 1 to 50, for example ranging from 1 to 10.

According to the present disclosure, the composition applied to the hair contains at least one volatile solvent. In the context of the present disclosure, the term "volatile solvent" means a compound that is liquid at room temperature (20° C.) and at atmospheric pressure, having a vapor pressure at 20° C. of greater than 0.1 mmHg, such as ranging from 0.1 to 300 mmHg, for example ranging from 0.5 to 200 mmHg.

This volatile solvent may be water, a non-silicone organic solvent, a silicone organic solvent, or mixtures thereof. Volatile non-silicone organic solvents of which non-limiting mention may be made include:

volatile C1-C4 alkanols such as ethanol or isopropanol;

volatile C5-C7 alkanes such as n-pentane, hexane, cyclopentane, 2,3-dimethylbutane, 2,2-dimethylbutane, 2-methylpentane, or 3-methylpentane;

esters of liquid C1-C20 acids and of volatile C1-C8 alcohols such as methyl acetate, n-butyl acetate, ethyl acetate, propyl acetate, isopentyl acetate, or ethyl 3-ethoxypropionate;

ketones that are liquid at room temperature and volatile, such as methyl ethyl ketone, methyl isobutyl ketone, diisobutyl ketone, isophorone, cyclohexanone, or acetone;

volatile polyols such as propylene glycol;

volatile ethers such as dimethoxymethane, diethoxyethane, or diethyl ether;

volatile glycol ethers such as 2-butoxyethanol, butyl diglycol, diethylene glycol monomethyl ether, propylene glycol n-butyl ether, or propylene glycol monomethyl ether acetate;

volatile hydrocarbon-based oils such as volatile hydrocarbon-based oils containing from 8 to 16 carbon atoms, and mixtures thereof, and, for example, branched C8-C16 alkanes, for instance C8-C16 isoalkanes (also known as isoparaffins), isododecane, isodecane and, for example, the oils sold under the trade names ISOPAR or PERMETHYL, and mixtures thereof. Non-limiting mention may also be made of isohexyl or isodecyl neopentanoate;

volatile C4-C10 perfluoroalkanes such as dodecafluoropentane, tetradecafluorohexane or decafluoropentane;

volatile perfluorocycloalkyls such as perfluoromethylcyclopentane, 1,3-perfluorodimethylcyclohexane, and perfluorodecalin, sold, respectively, under the names FLUTEC PC1®, FLUTEC PC3® and FLUTEC PC6® by the company F2 Chemicals, and also perfluorodimethylcyclobutane and perfluoromorpholine;

the volatile fluoroalkyl or heterofluoroalkyl compounds corresponding to the following formula:

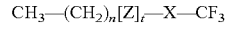

wherein t is 0 or 1; n is 0, 1, 2 or 3; X is a linear or branched divalent perfluoroalkyl radical containing from 2 to 5 carbon atoms, and Z is O, S or NR, R being hydrogen or a radical —(CH2)n—CH3 or —(CF2)m—CF3, m being 2, 3, 4, or 5.

The volatile fluoroalkyl or heterofluoroalkyl compounds that may be used include methoxynonafluorobutane sold under the names MSX 4518® and HFE-7100® by the company 3M, and ethoxynonafluorobutane sold under the name HFE-7200® by the company 3M.

For example, in at least one embodiment the at least one solvent may be chosen such that its boiling point is less than 200° C.

According to at least one embodiment of the present disclosure, the non-silicone organic solvent is chosen from ethanol, isopropanol, acetone, and isododecane.

Volatile silicone solvents that may be mentioned include low-viscosity silicone compounds chosen from linear or cyclic silicones containing from 2 to 7 silicon atoms, these silicones may comprise alkyl or alkoxy groups containing from 1 to 10 carbon atoms, for example octamethylcyclotetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane, decamethyltetrasiloxane, and mixtures thereof. According to at least one embodiment of the present disclosure, the silicone compound is chosen from cyclopentadimethylsiloxane and dodecamethylcyclohexasiloxane.

According to at least one embodiment of the present disclosure, the volatile silicone solvent has a viscosity of less than 50 centistokes.

For example, the volatile silicone may be cyclic and chosen from decamethylcyclopentasiloxane, octamethyltrisiloxane, and decamethyltetrasiloxane.

Examples of which non-limiting mention may be made include the decamethylcyclopentasiloxane sold under the name DC-245 by the company Dow Corning, the octamethyltrisiloxane sold under the name DC-200 FLUID 1 cSt by the company Dow Corning, and the decamethyltetrasiloxane sold under the name DC-200 FLUID 1.5 cSt by the company Dow Corning.

This cyclic volatile silicone generally has a low viscosity, for example a viscosity of less than 5 cSt at 25° C.

For example, the volatile silicone may be cyclic and is the decamethylcyclopentasiloxane sold under the name DC-245 by the company Dow Corning.

The at least one volatile solvent may be present in the composition according to the present disclosure in an amount ranging from 0.1% to 95% by weight, such as from 1% to 70% by weight, for example ranging from 5% to 90% by weight relative to the total weight of the composition.

The composition of the present disclosure may also contain at least one non-volatile organic solvent, such as:
  non-volatile aromatic alcohols such as benzyl alcohol or phenoxyethanol;
  esters of liquid C1-C20 acids and of non-volatile C1-C8 alcohols, such as isopropyl myristate;
  ethylene carbonate, propylene carbonate, or butylene carbonate;
  non-volatile polyols such as glycerol, ethylene glycol, dipropylene glycol, or butylene glycol;
  non-volatile glycol ethers, for instance diethylene glycol monomethyl ether or dipropylene glycol mono-n-butyl ether;
  non-volatile hydrocarbon-based oils such as isohexadecane;
  non-volatile liquid C10-C30 fatty alcohols such as oleyl alcohol; esters of liquid C10-C30 fatty alcohols such as benzoates of C10-C30 fatty alcohols and mixtures thereof; polybutene oil, isononyl isononanoate, isostearyl malate, pentaerythrityl tetraisostearate, or tridecyl trimellitate;
  non-volatile perfluoro solvents such as perfluoroperhydrophenanthrene, sold under the name FLUTEC PC11® by the company F2 Chemicals.

The composition according to the present disclosure comprises at least one pigment. Such a composition can make it possible to obtain colored and remanent coatings, without degradation of the keratin fibers.

As used herein, the term "pigment" means any pigment that gives keratin materials color, or white pigments such as titanium dioxide that give only white to keratin materials.

The at least one pigment that may be used can be chosen from the organic and/or mineral pigments known in the art, such as those described in Kirk-Othmer's Encyclopaedia of Chemical Technology and in Ullmann's Encyclopaedia of Industrial Chemistry.

The at least one pigment may be in the form of powder or of pigmentary paste. It may be coated or uncoated.

The at least one pigment may be chosen, for example, from mineral pigments, organic pigments, lakes, pigments with special effects such as nacres or glitter flakes, and mixtures thereof.

The at least one pigment may be a mineral pigment. As used herein, the term "mineral pigment" means any pigment that satisfies the definition in Ullmann's encyclopedia in the chapter on inorganic pigments. The mineral pigments that may be useful in the present disclosure include iron oxides, chromium oxides, manganese violet, ultramarine blue, chromium hydrate, and ferric blue.

The at least one pigment may be an organic pigment. As used herein, the term "organic pigment" means any pigment that satisfies the definition in Ullmann's encyclopedia in the chapter on organic pigments. For instance, the at least one organic pigment may be chosen from nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane, and quinophthalone compounds.

For example, the white or colored organic pigments may be chosen from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21100, 21108, 47000, and 47005, the green pigments codified in the Color Index under the references CI 61565, 61570, and 74260, the orange pigments codified in the Color Index under the references CI 11725, 15510, 45370, and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, and 75470, and the pigments obtained by oxidative polymerization of indole or phenolic derivatives as described in French Patent Publication No. FR 2 679 771.

Non-limiting examples that may also be mentioned include pigmentary pastes of organic pigments, such as the products sold by the company Hoechst under the names:
  JAUNE COSMENYL IOG: Pigment Yellow 3 (CI 11710);
  JAUNE COSMENYL G: Pigment Yellow 1 (CI 11680);
  ORANGE COSMENYL GR: Pigment Orange 43 (CI 71105);
  ROUGE COSMENYL R: Pigment Red 4 (CI 12085);
  CARMINE COSMENYL FB: Pigment Red 5 (CI 12490);
  VIOLET COSMENYL RL: Pigment Violet 23 (CI 51319);
  BLEU COSMENYL A2R: Pigment Blue 15.1 (CI 74160);
  VERT COSMENYL GG: Pigment Green 7 (CI 74260); and
  NOIR COSMENYL R: Pigment Black 7 (CI 77266).

The at least one pigment in accordance with the present disclosure may also be in the form of at least one composite pigment as described in European Patent Publication No. EP 1 184 426. These composite pigments may be, for example, compounds of particles comprising a mineral core, at least one binder for ensuring the binding of the organic pigments to the core, and at least one organic pigment at least partially covering the core.

The organic pigment may also be a lake. As used herein, the term "lake" means dyes adsorbed onto insoluble particles, the assembly thus obtained remaining insoluble during use.

The inorganic substrates onto which the dyes are adsorbed can be, for example, alumina, silica, calcium sodium borosilicate, calcium aluminum borosilicate, and aluminum.

Among the dyes, non-limiting mention may be made of cochineal carmine. Non-limiting mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), and D&C Blue 1 (CI 42 090).

A non-limiting example of a lake that may be mentioned is the product known under the following name: D&C Red 7 (CI 15 850:1).

The at least one pigment may also be a pigment with special effects. As used herein, the term "pigments with special effects" means pigments that generally create a non-uniform colored appearance (characterized by a certain shade, a certain vivacity, and a certain lightness) that changes as a function of the conditions of observation (light, temperature, observation angles, etc.). They thus contrast with white or colored pigments that afford a standard uniform opaque, semi-transparent, or transparent shade.

Several types of pigments with special effects exist: those with a low refractive index, such as fluorescent, photochromic, or thermochromic pigments, and those with a high refractive index, such as nacres or glitter flakes.

Examples of pigments with special effects of which non-limiting mention may be made include nacreous pigments such as mica coated with titanium or with bismuth oxychloride, colored nacreous pigments such as titanium mica with iron oxides, titanium mica for example with ferric blue or with chromium oxide, titanium mica with an organic pigment of the abovementioned type, and also nacreous pigments based on bismuth oxychloride. Nacreous pigments of which non-limiting mention may be made include the CELLINI nacres sold by Engelhard (mica-TiO$_2$-lake), PRESTIGE sold by Eckart (mica-TiO$_2$), PRESTIGE BRONZE sold by Eckart (mica-Fe$_2$O$_3$), and COLORONA sold by Merck (mica-TiO$_2$—Fe$_2$O$_3$).

In addition to nacres on a mica support, multilayer pigments based on synthetic substrates such as alumina, silica, sodium calcium borosilicate, calcium aluminum borosilicate, and aluminum, may be envisaged.

Non-limiting mention may also be made of pigments with an interference effect that are not fixed onto a substrate, for instance liquid crystals (HELICONES HC from Wacker) and holographic interference flakes (GEOMETRIC PIGMENTS or SPECTRA F/X from Spectratek). Pigments with special effects also comprise fluorescent pigments, whether these are substances that are fluorescent in daylight or that produce an ultraviolet fluorescence, phosphorescent pigments, photochromic pigments, thermochromic pigments, and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known from the literature. They may be manufactured, for example, according to the processes described, for example, in U.S. Pat. Nos. 6,225,198 or 5,990,479, in the publications cited therein, and also in the following publications: Dabboussi B. O. et al. "(CdSe)ZnS core-shell quantum dots: synthesis and characterization of a size series of highly luminescent nanocrystallites" *Journal of Physical Chemistry B*, vol. 101, 1997 pp. 9463-9475 and Peng, Xiaogang et al. "Epitaxial growth of highly luminescent CdSe/CdS core/shell nanocrystals with photostability and electronic accessibility", *Journal of the American Chemical Society*, vol. 119, No. 30, pp. 7019-7029.

The variety of pigments that may be used in the present disclosure makes it possible to obtain a wide range of colors, and also optical effects such as metallic effects or interference effects.

The size of the at least one pigment used in the cosmetic composition according to the present disclosure ranges from 10 nm to 200 µm, such as ranging from 20 nm to 80 µm, for example ranging from 30 nm to 50 µm.

The at least one pigment may be dispersed in the product via at least one dispersant.

The at least one dispersant serves to protect the dispersed particles against agglomeration or flocculation. The at least one dispersant may be a surfactant, an oligomer, a polymer, or a mixture of several thereof, bearing at least one functional group with strong affinity for the surface of the particles to be dispersed. For example, they can physically or chemically attach to the surface of the at least one pigment. These dispersants also contain at least one functional group that is compatible with or soluble in the continuous medium. For example, 12-hydroxystearic acid esters and C8 to C20 fatty acid esters of polyols such as glycerol or diglycerol are used, such as poly(12-hydroxystearic acid) stearate with a molecular weight of about 750 g/mol, such as the product sold under the name SOLSPERSE 21,000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof.

As other dispersants that may be used in the compositions of the present disclosure, non-limiting mention may be made of quaternary ammonium derivatives of polycondensed fatty acids, for instance SOLSPERSE 17,000 sold by the company Avecia, and polydimethylsiloxane/oxypropylene mixtures such as those sold by the company Dow Corning under the references DC2-5185 and DC2-5225 C.

The at least one pigment used in the cosmetic composition according to the present disclosure may be surface-treated with an organic agent.

Thus, the pigments that have been surface-treated beforehand, which are useful in the context of the present disclosure, are pigments that have totally or partially undergone a surface treatment of chemical, electronic, electrochemical, mechanochemical or mechanical nature, with an organic agent such as those described in, for example, Cosmetics and Toiletries, February 1990, Vol. 105, pp. 53-64, before being dispersed in the composition in accordance with the present disclosure. These organic agents may be chosen, for example, from amino acids; waxes, for example carnauba wax and beeswax; fatty acids, fatty alcohols, and derivatives thereof, such as stearic acid, hydroxystearic acid, stearyl alcohol, hydroxystearyl alcohol, lauric acid, and derivatives thereof; anionic surfactants; lecithins; sodium, potassium, magnesium, iron, titanium, zinc, or aluminum salts of fatty acids, for example aluminum stearate or laurate; metal alkoxides; polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes, and siloxysilicates; organofluorine compounds, for example perfluoroalkyl ethers; fluorosilicone compounds.

The surface-treated pigments that are useful in the cosmetic composition according to the present disclosure may also have been treated with a mixture of these compounds and/or may have undergone several surface treatments.

The surface-treated pigments that are useful in the context of the present disclosure may be prepared according to surface-treatment techniques that are well known to those skilled in the art, or may be commercially available in the required form.

For example, the surface-treated pigments may be coated with an organic layer.

The organic agent with which the pigments are treated may be deposited on the pigments by evaporation of solvent, chemical reaction between the molecules of the surface agent or creation of a covalent bond between the surface agent and the pigments. The surface treatment may thus be performed, for example, by chemical reaction of a surface agent with the surface of the pigments and creation of a covalent bond between the surface agent and the pigments or the fillers. This method is described in, for example, U.S. Pat. No. 4,578,266.

In at least one embodiment, an organic agent covalently bonded to the pigments may be used.

The agent for the surface treatment may be present in an amount ranging from 0.1% to 50% by weight, such as from 0.5% to 30% by weight, for example from 1% to 10% by weight relative to the total weight of the surface-treated pigments.

For example, the surface treatments of the pigments may be chosen from the following treatments:

a PEG-silicone treatment, for instance the AQ surface treatment sold by LCW;
a chitosan treatment, for instance the CTS surface treatment sold by LCW;
a triethoxycaprylylsilane treatment, for instance the AS surface treatment sold by LCW;
a methicone treatment, for instance the SI surface treatment sold by LCW;
a dimethicone treatment, for instance the Covasil 3.05 surface treatment sold by LCW;
a dimethicone/trimethyl siloxysilicate treatment, for instance the Covasil 4.05 surface treatment sold by LCW;
a lauroyllysine treatment, for instance the LL surface treatment sold by LCW;
a lauroyllysine dimethicone treatment, for instance the LL/SI surface treatment sold by LCW;
a magnesium myristate treatment, for instance the MM surface treatment sold by LCW;
an aluminum dimyristate treatment, for instance the MI surface treatment sold by Miyoshi;
a perfluoropolymethylisopropyl ether treatment, for instance the FHC surface treatment sold by LCW;
an isostearyl sebacate treatment, for instance the HS surface treatment sold by Miyoshi;
a disodium stearoyl glutamate treatment, for instance the NAI surface treatment sold by Miyoshi;
a dimethicone/disodium stearoyl glutamate treatment, for instance the SA/NAI surface treatment sold by Miyoshi;
a perfluoroalkyl phosphate treatment, for instance the PF surface treatment sold by Daito;
an acrylate/dimethicone copolymer and perfluoroalkyl phosphate treatment, for instance the FSA surface treatment sold by Daito;
a polymethylhydrogenosiloxane/perfluoroalkyl phosphate treatment, for instance the FS01 surface treatment sold by Daito;
a lauroyllysine/aluminum tristearate treatment, for instance the LL-AlSt surface treatment sold by Daito;
an octyltriethylsilane treatment, for instance the OTS surface treatment sold by Daito;
an octyltriethylsilane/perfluoroalkyl phosphate treatment, for instance the FOTS surface treatment sold by Daito;
an acrylate/dimethicone copolymer treatment, for instance the ASC surface treatment sold by Daito;
an isopropyl titanium triisostearate treatment, for instance the ITT surface treatment sold by Daito;
a microcrystalline cellulose and carboxymethylcellulose treatment, for instance the AC surface treatment sold by Daito;
a cellulose treatment, for instance the C2 surface treatment sold by Daito;
an acrylate copolymer treatment, for instance the APD surface treatment sold by Daito; and
a perfluoroalkyl phosphate/isopropyl titanium triisostearate treatment, for instance the PF+ITT surface treatment sold by Daito.

The composition in accordance with the present disclosure may further comprise at least one surface-untreated pigment.

For example, the at least one pigment may be a nacre.

The at least one pigment can be present in an amount ranging from 0.5% to 40%, such as from 1% to 20%.

The composition of the present disclosure may contain other colored or coloring species such as hydrophilic or hydrophobic direct dyes or dye precursors.

In order to obtain better spreading of the composition of the present disclosure and also improved coating, the composition of the present disclosure may also contain at least one polysiloxane having a viscosity of greater than 100 cSt, for example greater than 300 cSt. The viscosity of these polysiloxanes may be measured according to ASTM standard D-445. Such polysiloxanes may be silicone oils, gums or resins, or crosslinked silicones.

As polysiloxanes with a viscosity of greater than 100 cSt, non-limiting mention may be made of, for example, polydimethylsiloxanes; alkyl dimethicones; polyphenylmethylsiloxanes such as phenyl dimethicones, phenyl trimethicones, and vinyl methyl methicones; and also silicones modified with optionally fluorinated aliphatic and/or aromatic groups, or with functional groups such as hydroxyl, thiol and/or amine groups.

Such polysiloxanes can be chosen from the silicones of formula (I):

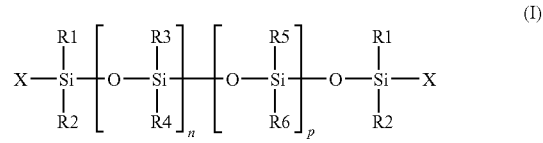

wherein:

R1, R2, R5, and R6 are, together or separately, an alkyl radical containing 1 to 6 carbon atoms, R3 and R4 are, together or separately, an alkyl radical containing from 1 to 6 carbon atoms, a vinyl radical, an aryl radical, an amine radical, or a hydroxyl radical, X is an alkyl radical containing from 1 to 6 carbon atoms, a hydroxyl radical, a vinyl radical, or an amine radical, n and p being integers chosen so as to obtain a viscosity of greater than 300 cSt.

Non-limiting examples that may be mentioned include the following polydimethylsiloxanes, wherein:
- the substituents R1 to R6 and X are methyl groups, such as the product sold under the name BAYSILICONE TP 3898 by the company General Electric, and the product sold under the name AK 500000 by the company Wacker,
- the substituents R1 to R6 and X are methyl groups, and p and n are such that the molecular weight is 120,000 g/mol, such as the product sold under the name DOW CORNING 200 FLUID 60000 CS by the company Dow Corning,
- the substituents R1 to R6 and X are methyl groups, and p and n are such that the molecular weight is 250,000 g/mol, for instance the product sold under the name MIRASIL DM 500,000 by the company Rhodia and the product sold under the name DOW CORNING 200 FLUID 500,000 cSt by the company Dow Corning,
- the substituents R1 to R6 are methyl groups, the group X is a hydroxyl group, and n and p are such that the molecular weight of the polymer is 600,000 g/mol, for instance the product sold under the name SGM 36 by the company Dow Corning, and
- dimethicones of the (polydimethylsiloxane)(methylvinylsiloxane) type, such as SE63 sold by GE Bayer Silicones, and poly(dimethylsiloxane)(diphenyl) (methylvinylsiloxane) copolymers, and mixtures thereof.

When the polysiloxane comprises a fluoro group, the at least one copolymer can have the structure:

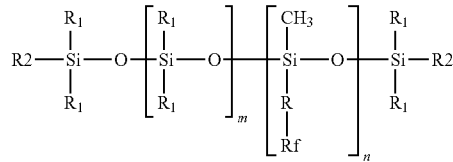

wherein:

R is a linear or branched divalent alkyl group containing 1 to 6 carbon atoms, for example a divalent methyl, ethyl, propyl, or butyl group, Rf is a fluoroalkyl radical, for example a perfluoroalkyl radical, containing 1 to 12 carbon atoms and, for example, 1 to 9 carbon atoms, R1 is, independently of each other, a C1-C20 alkyl radical, a hydroxyl radical, or a phenyl radical, R2 is R1 or Rf, m is chosen from 0 to 500, such as from 0 to 200, and n is chosen from 1 to 1,000, such as from 1 to 500.

For example, in at least one embodiment, the groups R1 are identical and are methyl radicals.

Such polysiloxanes include, for example, those sold by the company Shin-Etsu under the names FL-5, FL-10, X22-821, and X22-822 or FL-100 by the company Dow Corning, under the name FS-1265 FLUID by the company Phoenix Chemical, under the name PECOSIL FS or under the names PECOSIL FSL-150, PECOSIL FSL-300, PECOSIL FSH-150, PECOSIL FSH-300, PECOSIL FSU-150, and PECOSIL FSU-300.

The weight-average molecular mass of the polysiloxane may range from 1,000 to 1,500,000 g/mol, for example ranging from 20,000 to 1,000,000 g/mol.

The polysiloxane may be in the form of resin. As used herein, the term "resin" means a crosslinked or non-crosslinked three-dimensional structure. Non-limiting examples of polysiloxane resins include silsesquioxanes and siloxysilicates.

In at least one embodiment of the present disclosure, the polysiloxanes that are useful in the composition of the present disclosure are soluble or dispersible in the composition of the present disclosure. In at least one embodiment of the present disclosure, the silicone resin is solid at 25° C.

The composition of the present disclosure may also contain a crosslinked silicone such as a crosslinked elastomeric organopolysiloxane, a high molecular weight silicone compound of three-dimensional structure, having the viscoelastic properties of a supple solid material. These organopolysiloxanes may thus be in the form of dry powder, or in swollen form, in a solvent, the resulting product generally being a gel. These products may also be in dispersed form in an aqueous solution.

The synthesis of these organopolysiloxanes is described in, for example, the following patent publications:
- U.S. Pat. No. 5,266,321,
- U.S. Pat. No. 4,742,142,
- U.S. Pat. No. 5,654,362, and
- French Patent Application Publication No. FR 2 864 784.

The elastomeric organopolysiloxanes used in the composition may be partially or totally crosslinked. They are generally in the form of particles. For example, the elastomeric organopolysiloxane particles may have a number-average size ranging from 0.1 to 500 µm, such as from 3 to 200 µm, for example from 3 to 50 µm. These particles may have any shape and may be, for example, spherical, flat, or amorphous.

The crosslinked organopolysiloxane obtained may be a non-emulsifying compound or an emulsifying compound. As used herein, the term "non-emulsifying" means crosslinked organopolysiloxanes not containing polyoxyalkylene units. As used herein, the term "emulsifying" means crosslinked organopolysiloxane compounds having at least one polyoxyalkylene unit, such as polyoxyethylene or polyoxypropylene.

The crosslinked organopolysiloxane particles may be conveyed in the form of a gel comprised of a crosslinked organopolysiloxane included in at least one hydrocarbon-based oil and/or one silicone oil. In these gels, the organopolysiloxane particles are often non-spherical particles. The crosslinked organopolysiloxane particles may also be in the form of powder, such as in the form of spherical powder.

Non-emulsifying crosslinked organopolysiloxanes are, for example, described in U.S. Pat. Nos. 4,970,252; 4,987,169; 5,412,004; 5,654,362; and 5,760,116, and in Patent Application Publication No. JP-A-61-194009.

Non-emulsifying crosslinked organopolysiloxanes that may be used include those sold under the names KSG-6, KSG-15, KSG-16, KSG-18, KSG-31, KSG-32, KSG-33, KSG-41, KSG-42, KSG-43, KSG-44, and USG-103 by the company Shin-Etsu, DC9040, DC9041, DC9509, DC9505, DC9506, and DC9045 by the company Dow Corning, Gransil by the company Grant Industries, and SFE 839 by the company General Electric.

For example, the emulsifying crosslinked organopolysiloxanes may comprise polyoxyalkylene-modified organopolysiloxanes formed from divinyl compounds, such as polysiloxanes containing at least two vinyl groups, which react with Si—H bonds of a polysiloxane. The emulsifying crosslinked organopolysiloxanes are, for example, described in U.S. Pat. Nos. 5,236,986; 5,412,004; 5,837,793; and 5,811,487.

The emulsifying crosslinked organopolysiloxanes that may be used include those sold under the names KSG-21, KSG-20, KSG-30, and X-226146 by the company Shin-Etsu, and DC9010 and DC9011 by the company Dow Corning.

The elastomeric crosslinked organopolysiloxane particles may also be in the form of a powder of elastomeric crosslinked organopolysiloxane coated with silicone resin, such as with silsesquioxane resin, as described, for example, in U.S. Pat. No. 5,538,793.

Such elastomers are sold under the names KSP-100, KSP-101, KSP-102, KSP-103, KSP-104, and KSP-105 by the company Shin-Etsu.

When they are present, the amount of these silicone compounds ranges from 0.1% to 30% by weight, such as from 0.1% to 20% by weight, for example from 0.1% to 10% by weight.

The composition according to the present disclosure comprises at least one thickener chosen from polymeric thickeners and mineral thickeners.

The at least one thickener may be chosen from mineral and organic, and polymeric and non-polymeric thickener. The at least one thickener may be chosen to thicken an aqueous phase or a fatty phase of the composition, depending on the case.

As used herein, the term "thickener" means a compound that modifies the rheology of the medium into which it is incorporated.

For example, the aqueous-medium thickener may be chosen from:
- hydrophilic clays,
- hydrophilic fumed silica,
- water-soluble cellulose-based thickeners, such as hydroxyethylcellulose, methylcellulose or hydroxypropylcellulose. Among these, mention may be made, for example, of the gums sold under the name CELLOSIZE QP 4400H by the company Amerchol,
- nonionic guar gums comprising C1-C6 hydroxyalkyl groups. Non-limiting examples include hydroxymethyl, hydroxypropyl, and hydroxybutyl groups. Such guar gums are, for example, sold under the trade names JAGUAR HP8, JAGUAR HP60, JAGUAR HP120, and JAGUAR HP105 by the company Meyhall, or under the name GALACTASOL 40H4FD2 by the company Aqualon,
- carrageenans,
- carob gum, scleroglucan gum, gellan gum, rhamsan gum, or karaya gum,
- alginates, maltodextrins, starch, and derivatives thereof, hyaluronic acid, and salts thereof,
- the polyglyceryl(meth)acrylate polymers sold under the names HISPAGEL and LUBRAGEL by the companies Hispano Quimica or Guardian,
- polyvinylpyrrolidone,
- polyvinyl alcohol,
- crosslinked acrylamide polymers and copolymers, such as those sold under the names PAS 5161 or BOZEPOL C by the company Hoechst, SEPIGEL 305 by the company SEPPIC by the company Allied Colloid, or
- the crosslinked methacryloyloxyethyltrimethylammonium chloride homopolymers sold under the name SALCARE SC95 by the company Allied Colloid, and
- associative polymers, such as associative polyurethanes.

Such thickeners are, for example, described in European Patent Application Publication No. EP-A-1400 234.

The oily-medium thickener may be chosen from:
- organophilic clays;
- hydrophobic fumed silicas;
- alkyl guar gums (with a C1-C6 alkyl group), such as those described in European Patent Application Publication No. EP-A-708 114;
- oil-gelling polymers, for instance triblock polymers or star polymers resulting from the polymerization or copolymerization of at least one monomer containing an ethylenic group, for instance the polymers sold under the name KRATON;
- polymers with a weight-average molecular mass of less than 100,000, comprising a) a polymer backbone containing hydrocarbon-based repeating units containing at least one heteroatom, and optionally b) at least one pendent fatty chain and/or at least one terminal fatty chain, which are optionally functionalized, containing from 6 to 120 carbon atoms and being linked to these hydrocarbon-based units, as described in, for example, International Patent Application Publication Nos. WO-A-02/056847 and WO-A-02/47619, for example polyamide resins (such as those comprising alkyl groups containing from 12 to 22 carbon atoms) such as those described in U.S. Pat. No. 5,783,657;
- the silicone-based polyamide resins as described in European Patent Application Publication No. EP-A-1266 647 and in the French Patent Application No. 216 039.

Such thickeners are described in, for example, European Patent Application Publication No. EP-A-1400 234.

The thickener may be an organic gelling agent, i.e. an agent comprising at least one organic compound. The organogelling agents may be chosen from, for example, those described in International Patent Application Publication No. WO-A-03/105 788.

For example, the polymeric thickener present in the composition according to the present disclosure may be an amorphous polymer formed by polymerization of an olefin. The olefin may be an elastomeric ethylenically unsaturated monomer.

Non-limiting examples of olefins that may be mentioned include ethylenic carbide monomers, such as those containing one or two ethylenic unsaturations, and containing from 2 to 5 carbon atoms, such as ethylene, propylene, butadiene or isoprene.

The polymeric thickener is capable of thickening or gelling the composition. As used herein, the term "amorphous polymer" means a polymer that does not have a crystalline form. The polymeric thickener may also be film-forming.

The at least one polymeric thickener may be, for example, a diblock, triblock, multiblock, radial or star copolymer, or mixtures thereof.

Such polymeric thickeners are described in U.S. Patent Application Publication No. 2002/005562 and in U.S. Pat. No. 5,221,534.

For example, the polymeric thickener may be an amorphous block copolymer of styrene and of olefin.

The polymeric thickener may be hydrogenated to reduce the residual ethylenic unsaturations after the polymerization of the monomers.

For example, the polymeric thickener may be an optionally hydrogenated copolymer, containing styrene blocks and ethylene/C3-C4 alkylene blocks.

Diblock copolymers, for example hydrogenated, of which non-limiting mention may be made include styrene-ethylene/propylene copolymers and styrene-ethylene/butadiene copolymers. Diblock polymers are sold, for example, under the name KRATON® G1701E by the company Kraton Polymers.

Triblock copolymers, for example hydrogenated, of which non-limiting mention may be made include styrene-ethylene/propylene-styrene copolymers, styrene-ethylene/butadiene-styrene copolymers, styrene-isoprene-styrene copolymers, and styrene-butadiene-styrene copolymers. Triblock polymers are sold, for example, under the names KRATON® G1650, KRATON® G1652, KRATON® D1101, KRATON® D1102, and KRATON® D1160 by the company Kraton Polymers.

A mixture of styrene-butylene/ethylene-styrene triblock hydrogenated copolymer and of ethylene-propylene-styrene hydrogenated star polymer may also be used, such a mixture for instance, being in isododecane. Such mixtures are sold, for example, by the company Penreco under the trade names VERSAGEL® M5960 and VERSAGEL® M5670.

For example, a diblock copolymer such as those described previously, such as a styrene-ethylene/propylene diblock copolymer, may be used as polymeric thickener.

For example, the organophilic clays may be clays modified with chemical compounds that make the clay capable of swelling.

Clays are products that are already well known per se, which are described, for example, in the book *Minéralogie des argiles* [Clay mineralogy], S. Caillère, S. Hénin, M. Rautureau, $2^{nd}$ edition 1982, Masson, the teaching of which is included herein by way of reference.

Clays are silicates containing a cation that may be chosen from calcium, magnesium, aluminum, sodium, potassium, and lithium cations, and mixtures thereof.

Non-limiting examples of such products that may be mentioned include clays of the smectite family such as montmorillonites, hectorites, bentonites, beidellites, and saponites, and also of the family of vermiculites, stevensite, and chlorites.

These clays may be of natural or synthetic origin. For example, clays that are cosmetically compatible and acceptable with keratin materials may be used.

The organophilic clay may be chosen from montmorillonite, bentonite, hectorite, attapulgite, sepiolite, and mixtures thereof. The clay may be a bentonite or a hectorite.

These clays may be modified with a chemical compound chosen from quaternary amines, tertiary amines, amine acetates, imidazolines, amine soaps, fatty sulfates, alkyl aryl sulfonates, amine oxides, and mixtures thereof.

Organophilic clays of which non-limiting mention may be made include quaternium-18 bentonites such as those sold under the names BENTONE 3, BENTONE38, and BENTONE 38V by the company Rheox, TIXOGEL VP by the company United Catalyst, CLAYTONE 34, CLAYTONE 40, and CLAYTONE XL by the company Southern Clay; stearalkonium bentonites such as those sold under the names BENTONE 27 by the company Rheox, TIXOGEL LG by the company United Catalyst, and CLAYTONE AF and CLAYTONE APA by the company Southern Clay; quaternium-18/benzalkonium bentonites such as those sold under the names CLAYTONE HT and CLAYTONE PS by the company Southern Clay.

The fumed silicas may be obtained by high-temperature hydrolysis of a volatile silicon compound in an oxhydric flame, producing a finely divided silica. This process makes it possible to obtain hydrophilic silicas having a large number of silanol groups at their surface. Such hydrophilic silicas are sold, for example, under the names AEROSIL 130®, AEROSIL 200®, AEROSIL 255®, AEROSIL 300®, and AEROSIL 380® by the company Degussa, and CAB-O-SIL HS-5®, CAB-O-SIL EH-5®, CAB-O-SIL LM-130®, CAB-O-SIL MS-55®, and CAB-O-SIL M-5® by the company Cabot.

It is possible to chemically modify the surface of the silica, via a chemical reaction generating a reduction in the number of silanol groups. It is, for example, possible to substitute silanol groups with hydrophobic groups: a hydrophobic silica is then obtained.

The hydrophobic groups may be:
trimethylsiloxyl groups, which are obtained by treating fumed silica in the presence of hexamethyldisilazane. Silicas thus treated are known as "silica silylate" according to the CTFA (6th Edition, 1995). They are sold, for example, under the references AEROSIL R812® by the company Degussa and CAB-O-SIL TS-530® by the company Cabot;
dimethylsilyloxyl or polydimethylsiloxane groups, which are obtained by treating fumed silica in the presence of polydimethylsiloxane or dimethyldichlorosilane. Silicas thus treated are known as "silica dimethyl silylate" according to the CTFA (6th Edition, 1995). They are sold, for example, under the references AEROSIL R972® and AEROSIL R974® by the company Degussa and CAB-O-SIL TS-610® and CAB-O-SIL TS-720® by the company Cabot.

The fumed silica, for example, has a particle size that may be nanometric to micrometric, for example ranging from 5 to 200 nm.

An organomodified bentonite or hectorite may be used as mineral thickener.

The at least one thickener is present in the composition in a total amount ranging from 0.1% to 10% by weight, for example ranging from 0.5% to 7% by weight and such as ranging from 1% to 5% by weight relative to the total weight of the composition.

The compositions in accordance with the present disclosure may also contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, C10-C30 fatty acids such as stearic acid or lauric acid, and C10-C30 fatty amides such as lauric diethanolamide.

The at least one adjuvant can be present in an amount for each of them ranging from 0.01% to 20% by weight relative to the weight of the composition.

Needless to say, a person skilled in the art will take care to select this or these optional ingredient(s) such that the beneficial properties intrinsically associated with the formation of the coating in accordance with the present disclosure are not, or are not substantially, adversely affected.

The composition according to the present disclosure may be in, for example, the form of a suspension, a dispersion, a solution, a gel, an emulsion, such as an oil-in-water (O/W) or water-in-oil (W/O) emulsion, or a multiple emulsion (W/O/W or polyol/O/W or O/W/O), in the form of a cream, a mousse, a stick, a dispersion of vesicles, for example of ionic or nonionic lipids, a two-phase or multi-phase lotion, a spray, a powder or a paste. The composition may also be in the form of a lacquer.

A person skilled in the art can select the appropriate galenical form, and also the method for preparing it, on the basis of his general knowledge, taking into account firstly the nature of the constituents used, such as their solubility in the support, and also the intended use of the composition.

The composition may be an anhydrous composition, i.e. a composition containing less than 2% by weight of water, or even less than 0.5% water, for example free of water, the water not being added during the preparation of the composition, but corresponding to the residual water provided by the mixed ingredients.

The composition described above may be used on wet or dry hair, and also on any type of fair or dark, natural or dyed, permanent-waved, bleached or relaxed hair.

According to at least one embodiment of the process of the present disclosure, the hair is washed before application of the composition described above.

The application to the hair may be performed, for example, using a comb, a fine brush, a coarse brush, or the fingers.

The application of the composition is then followed by drying at a temperature above 40° C. According to at least one embodiment of the present disclosure, this temperature is greater than 45° C. According to at least one embodiment of the present disclosure, this temperature is greater than 45° C. and less than 220° C.

Drying may be performed immediately after the application or after a leave-on time that may range from 1 minute to 30 minutes.

For example, in addition to supplying heat, the hair may be dried using a flow of air. This flow of air during drying makes it possible to improve the individualization of the coating.

During drying, a mechanical action on the locks may be exerted, such as combing, brushing, or passing the fingers through.

The drying of the process of the present disclosure may be performed, for example, with a hood, a hairdryer, a smoothing iron, a Climazon, etc.

When the drying is performed with a hood or a hairdryer, the drying temperature ranges from 40 to 110° C., for example from 50 to 90° C.

When the drying step is performed with a smoothing iron, the drying temperature ranges from 110 to 220° C., for example from 140 to 200° C.

Once the drying is complete, a final rinse or shampoo wash may optionally be performed.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

EXAMPLES

Example 1

The following composition was prepared:

| | |
|---|---|
| Cellulose acetopropionate sold under the Reference CAB-381-0.5 by Eastman Chemical | 10 g |
| Mica-iron oxide nacre sold under the reference PRESTIGE SOFT BRONZE by Eckart | 10 g |
| Ethyl acetate | 80 g |

0.5 g of the composition was applied to a 1-g lock of clean, dry hair. The lock was immediately dried with a hairdryer heating the hair at a temperature of 80° C. for 1 minute, while combing constantly throughout the drying. A dyed lock whose hairs were individualized and whose color was shampoo-fast was obtained.

Example 2

The following composition was prepared:

| | |
|---|---|
| Copolymer of isobutyl methacrylate/bis-hydroxypropyl dimethicone acrylate at 40% in isododecane, sold by Grant Industries under the name GRANACRYSIL BMAS | 25 g |
| Mica-iron oxide nacre sold under the reference PRESTIGE SOFT BRONZE by Eckart | 10 g |
| α,ω-Dihydroxylated polydimethylsiloxane/cyclopentadimethylsiloxane (14.7/85.3) sold by Dow Corning under the name DC 1501 FLUID | 50 g |
| Isododecane | 15 g |

0.5 g of the composition was applied to a 1-g lock of clean, dry hair. After a leave-on time of 2 minutes, the lock was dried with a hairdryer heating the hair at a temperature of 80° C. for 2 minutes. A dyed lock whose hairs were individualized and whose color was shampoo-fast was obtained.

Example 3

The following composition was prepared:

| | |
|---|---|
| Acrylic acid/isobutyl methacrylate/ethyl methacrylate/n-tert-octylacrylamide copolymer sold under the reference DERMACRYL ® LT by the company National Starch | 10 g |
| Mica-iron oxide nacre sold under the reference PRESTIGE SOFT BRONZE by Eckart | 10 g |
| α,ω-Dihydroxylated polydimethylsiloxane/cyclopentadimethylsiloxane (14.7/85.3) sold by Dow Corning under the name DC 1501 FLUID | 40 g |
| Ethanol | 40 g |

0.5 g of the composition was applied to a 1-g lock of clean, dry hair. After a leave-on time of 2 minutes, the lock was dried with a hairdryer heating the hair at a temperature of 80° C. for 2 minutes, while brushing the lock during the drying. A dyed lock whose hairs were individualized and whose color was shampoo-fast was obtained.

Example 4

The following composition was prepared:

| | |
|---|---|
| DC245 FLUID sold by Dow Corning | 65 g |
| DC1501 FLUID sold by Dow Corning | 20 g |
| Nacre of mica coated with brown iron oxide, sold by Eckart under the name PRESTIGE BRONZE | 10 g |
| BIOPSA 7-4400 sold by Dow Corning | 5 g |

0.5 g of the composition was applied to a 1-g lock of clean, dry hair. After a leave-on time of 2 minutes, the lock was dried using a smoothing iron heating the hair at 180° C. A dyed lock whose hairs were individualized and whose color was shampoo-fast was obtained.

Example 5

The following composition was prepared:

| | |
|---|---|
| Isopropanol | 45 g |
| Cyclopentadimethylsiloxane sold by Dow Corning under the name DC245 FLUID | 30 g |
| Polydimethylsiloxane sold by Dow Corning under the reference DOW CORNING 200 FLUID 60000 cs | 5 g |
| Nacre of mica coated with brown iron oxide, sold by Eckart under the name PRESTIGE BRONZE | 10 g |
| Dimethylpolysiloxane/urea copolymer sold under the reference WACKER-BELSIL□ UD 60 by Wacker | 10 g |

0.5 g of the composition was applied to a 1-g lock of clean, dry hair. Without a leave-on time, the lock was dried with a hairdryer heating the hair at 80° C. at the maximum flow rate of air, while brushing the lock during the drying for 2 minutes. A dyed lock whose hairs were individualized and whose color was shampoo-fast was obtained.

Example 6

The following composition was prepared:

| | |
|---|---|
| Nacre of mica coated with brown iron oxide, sold by Eckart under the name PRESTIGE BRONZE | 10 g |
| Polymethylsilsesquioxane sold under the reference WACKER-BELSIL PMS MK Powder by Wacker | 10 g |
| Cyclopentadimethylsiloxane sold by Dow Corning under the name DC245 FLUID | 80 g |

0.5 g of the composition was applied to a 1-g lock of clean, dry hair. Without a leave-on time, the lock was dried with a hairdryer heating the hair at 80° C. at the maximum flow rate of air, while brushing the lock during the drying for 2 minutes. A dyed lock whose hairs were individualized and whose color was shampoo-fast was obtained.

Example 7

The following composition was prepared:

| | |
|---|---|
| Nacre of mica coated with brown iron oxide, sold by Eckart under the name PRESTIGE BRONZE | 10 g |
| Acrylates/C12-22 alkyl methacrylate copolymer as a 48% dispersion in water, sold by Rohm & Haas under the reference SOLTEX OPT | 20 g |
| 7-3100 Gum Blend HIP Emulsion sold by Dow Corning | 20 g |
| Water | 50 g |

0.5 g of the composition was applied to a 1-g lock of clean, dry hair. Without a leave-on time, the lock was dried with a hairdryer heating the hair at 8° C. at the maximum flow rate of air, while brushing the lock during the drying for 2 minutes. A dyed lock whose hairs were individualized and whose color was shampoo-fast was obtained.

What is claimed is:

1. A process for dyeing hair, comprising
applying to the hair at least one composition comprising at least one hydrophobic film-forming polymer, at least one pigment, and at least one volatile solvent, and
heating the hair covered with the composition at a temperature above 40° C. wherein
the at least one hydrophobic film-forming polymer is chosen from polymers and copolymers based on polyurethane, polyacrylate, silicone resins, polyurea/polyurethane silicones, and copolymers based on silicone resin and on dimethiconol.

2. The process according to claim 1, wherein the heating is performed at a temperature above 45° C.

3. The process according to claim 1, wherein the heating is performed at a temperature ranging from 45 to 200° C.

4. The process according to claim 1, wherein the at least one volatile solvent is chosen from water and at least one organic solvent chosen from ethanol, isopropanol, acetone, isododecane, decamethylcyclopentasiloxane, octamethyltrisiloxane, and decamethyltetrasiloxane.

5. The process according to claim 1, wherein the at least one hydrophobic film-forming polymer is present in an amount ranging from 0.1% to 40% by weight relative to the total weight of the composition.

6. The process according to claim 5, wherein the at least one hydrophobic film-forming polymer is present in an amount ranging from 0.5% to 20% by weight, relative to the total weight of the composition.

7. The process according to claim 6, wherein the at least one hydrophobic film-forming polymer is present in an amount ranging from 1% to 15% by weight, relative to the total weight of the composition.

8. The process according to claim 1, wherein the at least one volatile solvent is present in a total amount ranging from 0.1% to 95% by weight relative to the total weight of the composition.

9. The process according to claim 1, wherein the at least one pigment is present in an amount ranging from 1% to 40% by weight relative to the total weight of the composition.

10. The process according to claim 1, wherein the at least one pigment is chosen from nacres.

11. The process according to claim 1, wherein the composition further comprises at least one polysiloxane with a viscosity of greater than 300 cSt.

12. The process according to claim 1, wherein the heating is performed with a flow of air heating the hair at a temperature above 40° C.

* * * * *